US012807368B2

(12) United States Patent
Scavola et al.

(10) Patent No.: US 12,807,368 B2
(45) Date of Patent: Nov. 24, 2026

(54) AMPULE CRUSH TOOL

(71) Applicant: Verrica Pharmaceuticals Inc., West Chester, PA (US)

(72) Inventors: Eugene R. Scavola, Charlottesville, VA (US); Paul Daly, Plymouth, NH (US); Gregory Alcorn, Valley Forge, PA (US); Vicki Fluck, Quakertown, PA (US)

(73) Assignee: Verrica Pharmaceuticals Inc., West Chester, PA (US)

( * ) Notice: Subject to any disclaimer, the term of this patent is extended or adjusted under 35 U.S.C. 154(b) by 513 days.

(21) Appl. No.: 18/032,266

(22) PCT Filed: Oct. 13, 2021

(86) PCT No.: PCT/US2021/054752

§ 371 (c)(1),
(2) Date: Apr. 17, 2023

(87) PCT Pub. No.: WO2022/086773

PCT Pub. Date: Apr. 28, 2022

(65) Prior Publication Data

US 2023/0399217 A1 Dec. 14, 2023

Related U.S. Application Data

(60) Provisional application No. 63/094,231, filed on Oct. 20, 2020.

(51) Int. Cl.
*A61J 1/06* (2006.01)
*A61M 35/00* (2006.01)
(Continued)

(52) U.S. Cl.
CPC .............. *B65D 17/50* (2013.01); *A61J 1/065* (2013.01); *A61M 35/003* (2013.01); *B05C 1/04* (2013.01); *B67B 7/92* (2013.01)

(58) Field of Classification Search
CPC .... A61J 1/065; A61M 35/003; A61M 35/006; B65D 81/3277; B65D 47/42; B67B 7/92
See application file for complete search history.

(56) References Cited

U.S. PATENT DOCUMENTS 2,232,978 A 2/1941 Smith
2,297,335 A 9/1942 Wheaton, Jr.
(Continued)

FOREIGN PATENT DOCUMENTS

CN 201058808 Y 5/2008
CN 102497908 A 6/2012
(Continued)

OTHER PUBLICATIONS

International Search Report and Written Opinion, mailed Mar. 1, 2022 for International Application No. PCT/US2021/054752.
(Continued)

*Primary Examiner* — Jessica Arble
(74) *Attorney, Agent, or Firm* — Wolf, Greenfield & Sacks, P.C.

(57) ABSTRACT

Tools (100) for crushing an ampule (146) contained within an applicator (102) for a therapeutic are disclosed herein. The ampule crush tool may be configured to rest on an incline relative to a flat surface. Further, the ampule crush tool may include a spill reservoir (122) for collecting a volume of the therapeutic expelled during an ampule crushing operation. Additionally, the ampule crush tool may form a fully enclosed cavity such that the ampule crush tool may contain the therapeutic even when the therapeutic is expelled from the ampule along an unpredictable trajectory. The ampule crush tool may also be shaped to orient an ampule-containing applicator in a suitable orientation within the ampule crush tool.

16 Claims, 7 Drawing Sheets

(51) Int. Cl.

| | |
|---|---|
| ***B05C 1/04*** | (2006.01) |
| ***B65D 17/50*** | (2006.01) |
| ***B67B 7/92*** | (2006.01) |

(56) References Cited

U.S. PATENT DOCUMENTS

| | | | | |
|---|---|---|---|---|
| 4,210,142 | A | 7/1980 | Worder | |
| 4,353,869 | A | 10/1982 | Guth | |
| 4,405,067 | A * | 9/1983 | Caron | B67B 7/92 225/93 |
| 4,417,679 | A | 11/1983 | Shields | |
| 4,432,768 | A * | 2/1984 | Brown | B67B 7/92 604/200 |
| 4,637,139 | A * | 1/1987 | Chen | B67B 7/92 241/606 |
| 4,805,821 | A | 2/1989 | Kowalczyk et al. | |
| 4,957,385 | A * | 9/1990 | Weinstein | A61M 35/006 604/3 |
| D312,876 | S | 12/1990 | Spock | |
| D330,598 | S | 10/1992 | Bottner | |
| 5,538,353 | A | 7/1996 | DeHavilland | |
| D375,788 | S | 11/1996 | Potts et al. | |
| 6,022,339 | A | 2/2000 | Fowles et al. | |
| 6,582,415 | B1 | 6/2003 | Fowles et al. | |
| 6,613,022 | B1 | 9/2003 | Doyle | |
| D613,872 | S | 4/2010 | Carota et al. | |
| D628,061 | S | 11/2010 | Nakano | |
| 8,173,418 | B2 * | 5/2012 | Sestak | C12M 37/06 435/31 |
| 8,448,830 | B2 | 5/2013 | Starr | |
| D900,312 | S | 10/2020 | Davidson et al. | |
| 11,241,690 | B2 | 2/2022 | Noguchi et al. | |
| 2002/0076255 | A1 * | 6/2002 | Hoang | A61M 35/003 401/133 |
| 2003/0111552 | A1 | 6/2003 | Vedrine et al. | |
| 2006/0039742 | A1 | 2/2006 | Cable et al. | |
| 2006/0049203 | A1 | 3/2006 | Boone et al. | |
| 2008/0058863 | A1 | 3/2008 | Quintero et al. | |
| 2008/0298879 | A1 | 12/2008 | Chesak et al. | |
| 2009/0311739 | A1 | 12/2009 | Sestak et al. | |
| 2010/0010434 | A1 | 1/2010 | Oyama | |
| 2010/0065049 | A1 | 3/2010 | Farieta et al. | |
| 2011/0066121 | A1 | 3/2011 | Hoang et al. | |
| 2012/0103202 | A1 | 5/2012 | Hensel | |
| 2012/0103203 | A1 * | 5/2012 | Hensel | A47J 43/0761 99/504 |
| 2012/0208285 | A1 | 8/2012 | Deighan et al. | |
| 2012/0224387 | A1 | 9/2012 | Moore | |
| 2015/0216234 | A1 | 8/2015 | Chung | |
| 2016/0166816 | A1 | 6/2016 | Mingione et al. | |
| 2018/0092807 | A1 | 4/2018 | Brandenburger | |
| 2018/0177993 | A1 | 6/2018 | Fitzgerald et al. | |
| 2019/0015297 | A1 | 1/2019 | Harada et al. | |
| 2019/0159969 | A1 | 5/2019 | Porter et al. | |
| 2020/0385181 | A1 * | 12/2020 | Hiemer | B65D 47/36 |
| 2021/0138214 | A1 | 5/2021 | Davidson et al. | |

FOREIGN PATENT DOCUMENTS

| | | | |
|---|---|---|---|
| CN | 105769349 | A | 7/2016 |
| CN | 107051764 | A | 8/2017 |
| EP | 1445032 | A2 | 8/2004 |
| FR | 1558035 | A | 2/1969 |
| GB | 6131719 | | 4/2021 |
| HK | 2117857-0002 | | 4/2021 |
| IN | 201717045844 | A | 2/2018 |
| JP | 2004-337837 | A | 12/2004 |
| WO | WO 2016/144151 | A1 | 9/2016 |

OTHER PUBLICATIONS

International Preliminary Report on Patentability, mailed May 4, 2023 for International Application No. PCT/US2021/054752.

[No Author Listed], Health Care 7371 Ampule Opener. Amazon. Date First Available Jul. 6, 2016. Accessed Apr. 9, 2022 from <https://www.amazon.com/Health-Care-7371-Ampule-Opener/dp/B00HYUN2W2/ref=sr_1_6?crid=2TYUY73PVFKAX&keywords=ampule+cutter+opener&qid=1649529532&sprefix=ampule+c%2Caps%2C192&sr=8-6>. 4 pages.

[No Author Listed], SnapIT—Instructions for Use. YouTube Screenshot. Date First Uploaded Aug. 8, 2011. Accessed Apr. 8, 2022 from <https://www.youtube.com/watch?v=Od5WShZIOoy>. 1 page.

[No Author Listed], Wheaton Science Products 177105 Plastic Ampule Snapper for 1 mL and 2 mL Ampule (Pack of 144). Amazon. Date First Available Mar. 20, 2008. Accessed Apr. 9, 2022 from <https://www.amazon.com/Wheaton-Science-Products-Plastic-Snapper/dp/B01HIQ4EW8/ref=sr_1_25?crid=3JJI849C9RF3Q&keywords=ampule+opener&qid=1649533698&sprefix=ampule+opene%2Caps%2C85&sr=8-25>. 4 pages.

[No Author Listed], Multifunctional Ampoule Opener. YouTube Screenshot. Date First Uploaded Sep. 28, 2018. Accessed Apr. 8, 2022 from <https://www.youtube.com/watch?v=4kOrDXPJNvU>. 1 page.

* cited by examiner

AMPULE CRUSH TOOL

CROSS-REFERENCE TO RELATED APPLICATIONS

This application is a national stage filing under 35 U.S.C. § 371 of International Application No. PCT/US2021/054752, filed Oct. 13, 2021, which claims the benefit of U.S. Provisional Application No. 63/094,231, filed Oct. 20, 2020. The contents of these applications are incorporated herein by reference in their entirety.

FIELD

Disclosed embodiments relate to an ampule crush tool, for example, an ampule crush tool for preparing a medicament applicator for use.

BACKGROUND

The body surfaces of the body can be affected by various disorders. For example, many cutaneous disorders produce lesions on the skin. Some of these lesions take the form of epidermal growths on the skin. For instance, warts are small epidermal skin growths caused by viral infections, often found on the hands or feet. The most common type of wart is called Verruca vulgaris, which can be caused by multiple different strains of the human papilloma virus (HPV). On most parts of the body these warts may be referred to as common warts; on the feet, however, they may be referred to as plantar warts; when on the genitals they may be referred to as genital warts or condoloma. Other epidermal viral conditions such as Molluscum contagiosum resemble warts but are caused by distinct viruses. These viral mediated skin growths may be unsightly and may pose a significant risk for cancerous transformation and for spreading, making their removal desirable. Other superficial hyperproliferative disorders resemble warts but are caused by non-viral mechanisms and include seborrheic keratosis, actinic keratosis, and porokeratosis.

Multiple modalities have been used to remove warts, Molluscum contagiosum, and other cutaneous diseases, including cryotherapy; surgical curettage; laser treatment; irritants such as salicylic acid and zinc oxide; acids such as nitric acid and squaric acid, immunotherapeutics such as imiquimod, 2,4-dinitrochlorobenzene and *Candida* antigen, and chemotherapeutics such as bleomyocin, podophyllotoxin and 5-fluorouracil. Many of these therapies can be painful, while others can leave disfiguring scars and/or require daily application. Many of these cutaneous disorders remain recalcitrant even after multiple follow-up treatments. Accordingly, improved therapies are needed for treating these conditions.

SUMMARY

In some embodiments, an ampule fracture device includes a body having a first end and a second end, and a support configured to incline the first end of the body at a first height vertically above a second height of the second end of the body when the ampule fracture device is rested on a flat surface and while the device is actuated to fracture an ampule.

In some embodiments, a method of fracturing an ampule includes (1) placing a tool on a flat surface, (2) placing a medicament applicator having an ampule within a cavity of the tool, and (3) actuating the tool to fracture the ampule while the tool holds the medicament applicator at an inclined angle relative to the flat surface.

In some embodiments, an ampule fracture device includes a body having a first end and a second end, and a cavity disposed on the first end of the body, the cavity configured to receive at least a distal end of a medicament applicator, the distal end including a dispenser tip, wherein the cavity includes a sidewall and a reservoir that is recessed relative to the sidewall, the reservoir being configured to collect a medicament expelled from an ampule during an ampule fracturing operation.

In some embodiments, a method of fracturing an ampule includes (1) placing a medicament applicator having an ampule within a cavity of a tool, (2) fracturing the ampule with the tool, causing medicament from the ampule to be expelled out of the medicament applicator, and (3) collecting the expelled medicament within the cavity.

In some embodiments, an ampule fracture device includes a base portion having a first cavity, and a cover portion having a second cavity, wherein the cover portion and the base portion are moveable relative to one another to form an open configuration and a closed configuration, wherein, in the closed configuration, the cover portion covers the base portion, and the first cavity and the second cavity form a closed enclosure.

In some embodiments, an ampule fracture device includes a cavity configured to receive a medicament applicator having an ampule, wherein the cavity includes a first portion and a second portion, the first portion shaped and positioned to receive a dispensing end of the medicament applicator, and the second portion shaped and positioned to receive a tube end of the medicament applicator, the first portion having a tapered shape, and the second portion having a cylindrical shape.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

To treat various body surface disorders, a clinician may employ one or more of a number of suitable therapeutics. Therapeutics for treating such disorders may include ointments, creams, or other suitable therapeutics, which may be applied to the skin of a patient. In some instances, the clinician may apply a therapeutic to a patient using a wooden stick, for example, when the therapeutic is contained within a jar.

In other instances, the clinician may apply the therapeutic using an applicator which may contain the therapeutic in a breakable ampule made from glass, plastic, or any other suitable material. One example of such an applicator is discussed in U.S. application Ser. No. 16/621,854, published as U.S. Patent Application Publication No. US 2021/0138214, also published as WO 2018/232277, each of which is incorporated by reference herein.

Figure 1A:
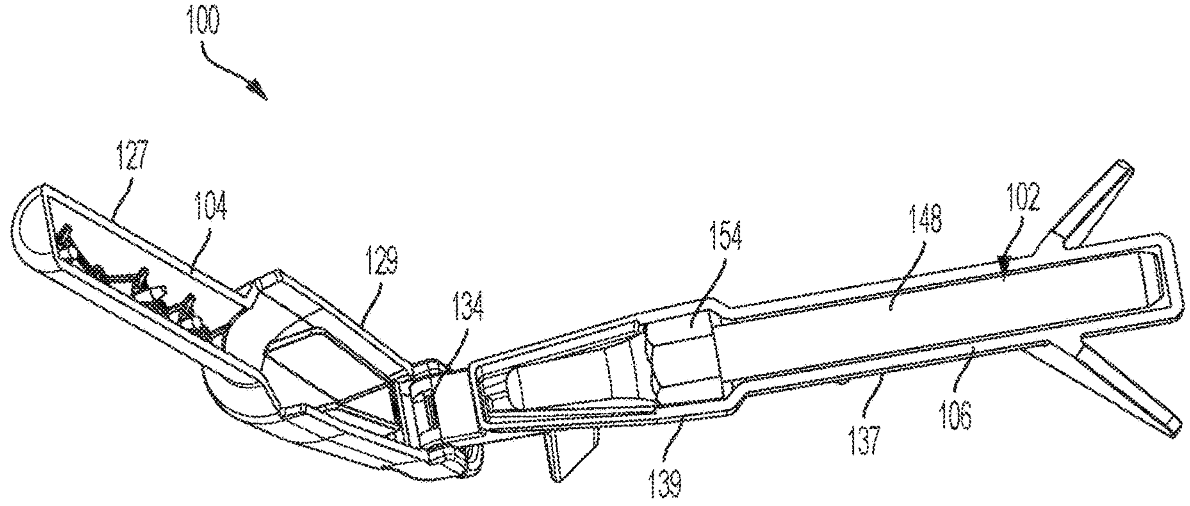
FIG. 1A is a perspective view of an ampule crush tool holding an applicator, the ampule crush tool being in an open configuration according to one illustrative embodiment.
Figure 2:
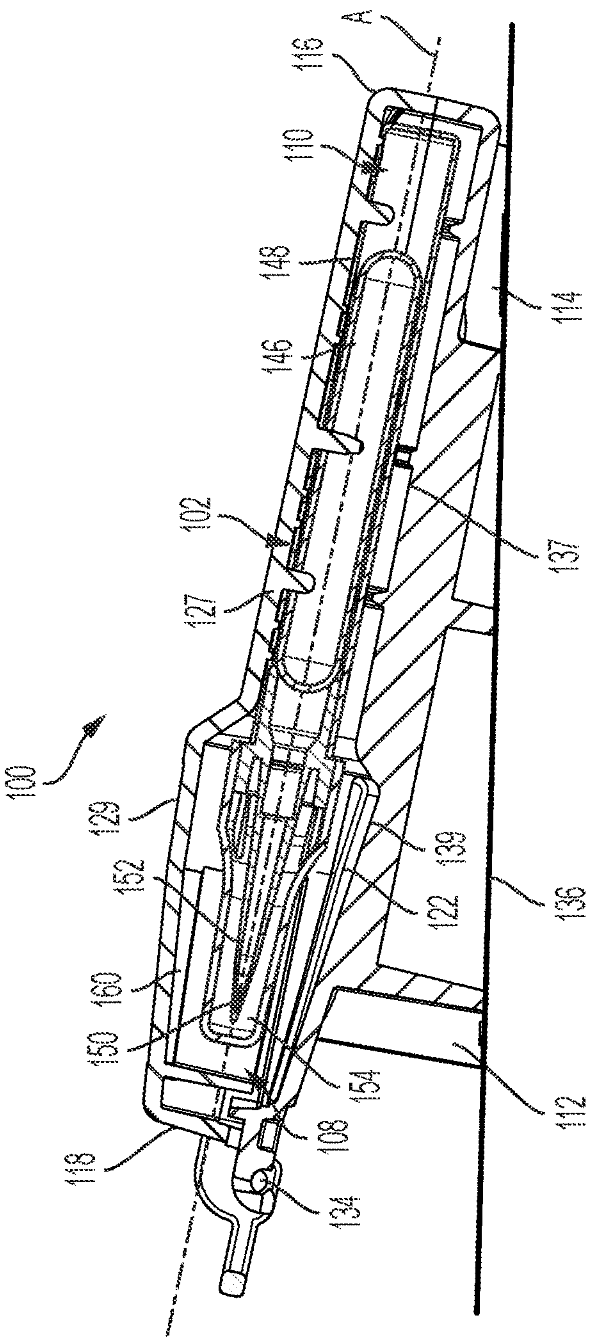
FIG. 2 is a cross sectional side view of an ampule crush tool holding an applicator according to one illustrative embodiment.

One illustrative embodiment of an applicator 102 is shown in FIG. 1A, and a cross-section of the applicator 102 is shown in FIG. 2. The applicator 102 may include an ampule 146 and an outer tube 148, where the ampule is located within the outer tube. The applicator 102 may also include a dispenser tip 152 with an outlet 150. The applicator may also include a cap 154 that may cover the outlet 150 of the dispenser tip 152.

In instances where the clinician uses such an applicator, the ampule contained within the applicator may be crushed prior to use in order to release the therapeutic contained within the ampule for administration to a patient. In some instances, the ampule may be difficult to break by hand. Accordingly, the inventors have recognized that need for a tool to assist with breaking the ampule contained within an applicator.

In view of the above, the inventors have recognized the advantages of an ampule crush tool to prepare an applicator for use by breaking the ampule contained within the applicator.

The applicator may include a dispenser tip and a cap that covers the dispenser tip. In some embodiments, the cap may not form an airtight seal. In some embodiments, a cap may be purposefully designed not to form an airtight seal, depending on the application. For example, in some instances, the cap may be designed to permit venting through the cap to allow the dispenser tip of the applicator to self-seal. Specifically, after being exposed to air for a period of time, at least a portion of the therapeutic (e.g., a portion of the therapeutic positioned towards an outlet in the dispenser tip) may harden over time. The hardened therapeutic may block the outlet of the dispenser tip, enabling a self-sealing effect, and may prevent the therapeutic from flowing out of the dispenser tip. The self-sealing effect may be caused by evaporation of solvent (e.g., water or alcohol) from the therapeutic, which may leave behind a solid, enabling the self-sealing effect. The self-sealing effect may serve as a tamper-evident seal, or the self-sealing feature may help to prevent degradation or oxidation of the therapeutic. In some cases, the clinician may remove the cap of the applicator prior to crushing the ampule and may proceed to crush the ampule while the cap is removed. Thus, in some instances (e.g., instances where the cap of the applicator does not form an air tight seal and/or instances where the clinician removes the cap of the applicator prior to crushing and proceeds to crush the ampule with the cap removed), the act of using the ampule crush tool to crush the ampule contained within the applicator may cause a volume of the therapeutic contained within the applicator to be displaced towards an outlet of the applicator (e.g., a dispenser tip) and thus, expelled from the applicator. Accordingly, the inventors have further recognized the advantages of an ampule crush tool capable of minimizing the volume of the therapeutic expelled when the ampule is crushed.

In some instances, the clinician may wish to prevent unwanted exposure to the therapeutic. Thus, the inventors have also recognized the advantages of an ampule crush tool capable of containing the volume of the therapeutic expelled from the applicator when the ampule is crushed.

Embodiments disclosed herein relate to an ampule crush tool constructed to accommodate an applicator for applying a therapeutic to a patient. In some embodiments, the ampule crush tool includes features for preventing a volume of the therapeutic from being expelled from the applicator during an ampule crushing operation and features for containing a volume of the therapeutic expelled from the applicator during the crushing operation.

An ampule crush tool according to the present disclosure may include two portions movable relative to one another, such as a cover portion and a base portion. The cover and base portion may be movable relative to one other via a hinge (e.g., a living hinge, a pivot hinge, a pin hinge, a case hinge, a concealed hinge or other suitable type of hinge). In some embodiments, the cover portion and the base portion are formed as a single continuous piece with a living hinge, while in other embodiments, the cover portion and the base portion are formed as two separate pieces (e.g. with a hinge connecting the two separate pieces). The combination of the cover and base portions may be constructed to accommodate an ampule-containing applicator, wherein the ampule holds a therapeutic. The cover and/or base portions may include one or more ribs for crushing the ampule. For example, the cover portion may include one or more ribs such that when the applicator is placed in the ampule crush tool and the cover portion is pressed over the base portion, or the cover portion and base portion are otherwise moved toward one another, the ribs serve to fracture the ampule contained within the applicator. Conversely, the base portion may include one or more ribs such that when the applicator is placed in the ampule crush tool and the cover portion is pressed over the base portion, or the cover portion and the base portion are otherwise moved toward one another, the ribs serve to fracture the ampule contained within the applicator. Of course, the one or more ribs need not be disposed on either the base portion or the cover portion. For example, both the base portion and the cover portion may include one or more ribs. Alternatively, a plurality of ribs may be interspersed between the cover portion and the base portion, for example, in an alternating pattern. As will be appreciated by one of skill in the art, any suitable arrangement of ribs may be employed.

To perform an ampule crushing operation (e.g., use the ampule crush tool to crush the ampule contained within the applicator), the clinician may begin by opening the cover portion, allowing the clinician to insert the applicator into the ampule crush tool. The clinician may then place the applicator within the ampule crush tool, for example, such that the applicator nests within the base portion. After placing the applicator within the base portion, the clinician may then close the cover portion to fracture the ampule contained within the applicator (e.g., via the ribs described above). After fracturing the ampule, the clinician may then reopen the cover portion and remove the applicator, which is prepared for use with a patient. Thus, the clinician may then apply the therapeutic contained within the applicator to the patient.

In some embodiments, the ampule crush tool includes features for preventing the therapeutic from being expelled from the applicator while the ampule crush tool is used to crush the therapeutic-containing ampule housed within the applicator. For example, the ampule crush tool may include one or more supports configured to position the ampule crush tool, and by extension the applicator contained within the ampule crush tool, at an incline during the crushing operation. In some embodiments, an ampule crush tool includes one or more supports attached to a body (e.g., a base portion). A support may be positioned on a first end of the body of the ampule crush tool such that the first end sits vertically higher than a second end of the body of the ampule crush tool (i.e., the end opposite from the first end) when the ampule crush tool rests on a flat surface. Thus, the support may serve to incline the ampule crush tool relative to the surface. As will be appreciated from the above, the applicator, which may fit into the ampule crush tool in an orientation substantially parallel to the ampule crush tool, may also be inclined along with the body of the ampule crush tool. In some instances, the outlet of the applicator may be positioned towards the first end of the ampule crush tool. Thus, the outlet of the applicator may be positioned at a height that is vertically higher than the portion of the applicator containing the therapeutic (e.g., the ampule). Accordingly, as the ampule contained within the applicator is crushed, the inclined orientation may serve to allow gravity to pull the therapeutic away from the outlet of the applicator, allowing the therapeutic to settle toward the end of the applicator opposite to the outlet end. In some cases, the inclined support of the ampule crush tool may serve to prevent the therapeutic from being expelled or decrease the amount of therapeutic expelled from the applicator during an ampule crushing operation.

Nevertheless, in some instances, a volume of the therapeutic may be expelled from the applicator during the ampule crushing operation. Thus, the ampule crush tool may include features that allow the ampule crush tool to collect the volume of the therapeutic expelled from the applicator during the ampule crushing operation. For example, in some embodiments, the ampule crush tool includes a spill reservoir constructed to collect the volume of the therapeutic expelled during the ampule crushing operation. The spill reservoir may be disposed on the first end of the ampule crush device (i.e., the end constructed to accommodate the outlet of the applicator). The spill reservoir may be formed within a cavity of the body of the ampule crush tool. The cavity may include a sidewall, and the spill reservoir may be indented relative to the sidewall of the cavity. In some embodiments, the ampule crush tool may include a splash shield constructed to direct the volume of the therapeutic expelled during the ampule crushing operation towards the spill reservoir. Thus, the spill reservoir may collect the volume of the therapeutic expelled during the ampule crushing operation, preventing unwanted exposure to the therapeutic.

In some instances, the volume of the therapeutic expelled from the applicator during the ampule crushing operation may leave the applicator along an unpredictable trajectory. Thus, the ampule crush tool may also include features for containing all of the therapeutic expelled from the applicator during the ampule crushing operation. For example, the cover portion and the base portion may be constructed such that the cover portion is movable relative to the base portion between an open configuration and a closed configuration. In the open configuration, the cover portion may be sufficiently distant from the base portion such that the applicator may be placed into the ampule crush tool. Conversely, in the closed configuration, the cover portion may fully cover the base portion such that the combination of the cover portion and the base portions forms a complete enclosure. In some embodiments, the cover portion and the base portion may each include an extended sidewall such that the extended sidewall of the cover portion overlaps with the extended sidewall of the case portion. In some embodiments, the overlap may form a seal. Thus, the ampule fracture tool may further prevent unwanted exposure to the therapeutic, as the seal may help contain the volume of the therapeutic expelled during the ampule crushing operation within the ampule crush tool.

In some embodiments, the ampule crush tool may include features that allow the ampule crush tool to hold the applicator in a predetermined orientation. For example, the ampule fracture tool may include a cavity constructed to accommodate the applicator. The cavity may include a first portion and a second portion. The first portion may be shaped to receive a dispensing end of the applicator (i.e., the end containing the outlet of the applicator), while the second end may be shaped to receive a tube end of the applicator (i.e., the end containing the ampule). To that end, the first portion of the cavity may have a tapered shape, while the second portion of the cavity may have a cylindrical shape. Thus, the cavity of the ampule crush tool may be shaped to hold the applicator in an orientation where the dispensing end of the applicator is held on the first end of the ampule crush tool and the tube end of the applicator is held on the second end of the ampule crush tool.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1B:
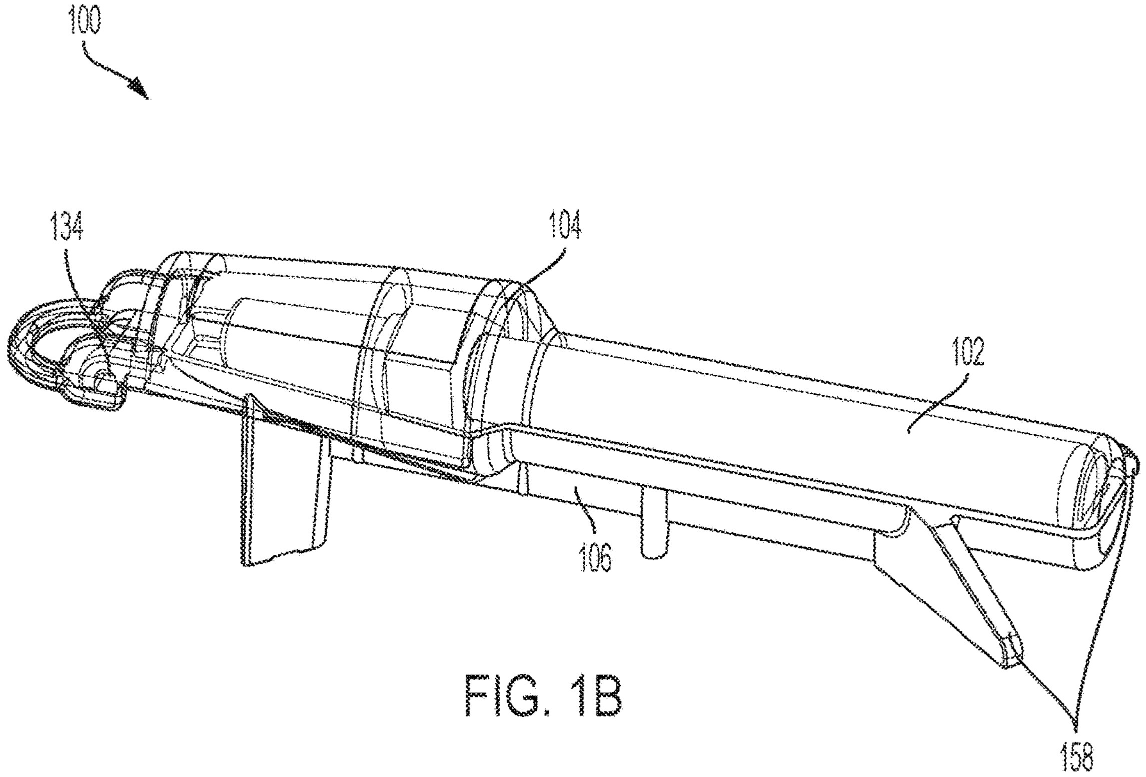
FIG. 1B is a perspective view of the ampule crush tool of FIG. 1A in a closed configuration, with a cover portion of the ampule crush tool shown in phantom.

FIG. 1A is a perspective view of an ampule crush tool 100 in an open configuration, and FIG. 1B is a perspective view of ampule crush tool 100 in a closed configuration. As will be appreciated from FIGS. 1A-1B, ampule crush tool 100 may include a cover portion 104 and a base portion 106. In FIG. 1B, the cover portion 104 is shown in phantom to reveal an applicator 102 held within the base portion 106. In the open configuration, cover portion 104 may be disposed a distance away from base portion 106, while in the closed configuration, cover portion 104 may be flush with or overlapping with base portion 106. Cover portion 104 and base portion 106 may be movable relative to one another via a hinge 134. Thus, when cover portion 104 is moved relative to base portion 106 such that ampule crush tool 100 is in the open configuration, an applicator 102 (e.g., an applicator containing an ampule of a therapeutic) may be placed within the base portion 106 of ampule crush tool 100. Ampule crush tool 100 may then be placed in the closed configuration by moving cover portion 104 towards base portion 106 with applicator 102 inside of ampule crush tool 100. The act of transitioning ampule crush tool 100 from the open configuration to the closed configuration may serve to crush the ampule disposed within applicator 102, as described in greater detail below. In some embodiments, the ampule crush tool may be moved between the open configuration and the closed configuration by moving the cover portion toward and away from the base portion, by moving the base portion toward and away from the cover portion, or a combination of both.

In some embodiments, the ampule crush tool may have a tubular portion for receiving a tube portion of an applicator, and may have a second portion for receiving a dispensing end of an applicator (e.g., the cap end of an applicator and/or a dispenser tip of an applicator). In some embodiments, the second portion may flare out relative to the tubular portion, e.g. to accommodate the cap and/or dispenser tip of the applicator. In the illustrative embodiment of FIG. 1A, the tubular portion is formed from tubular portion 137 of the base portion 106 and tubular portion 127 of the cover portion 104. The second portion is formed from the flared portion 139 of the base portion 106 and the flared portion 129 of the cover portion 104.

Figure 4A:
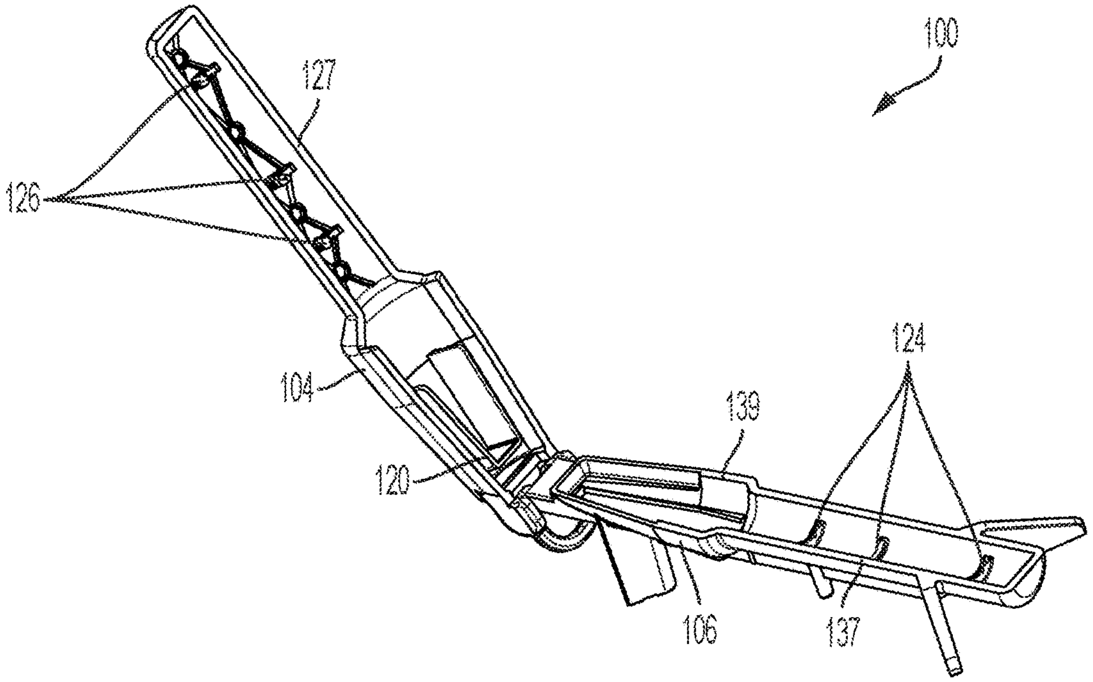
FIG. 4A is a perspective view of an ampule crush tool in an open configuration according to one illustrative embodiment.
Figure 4B:
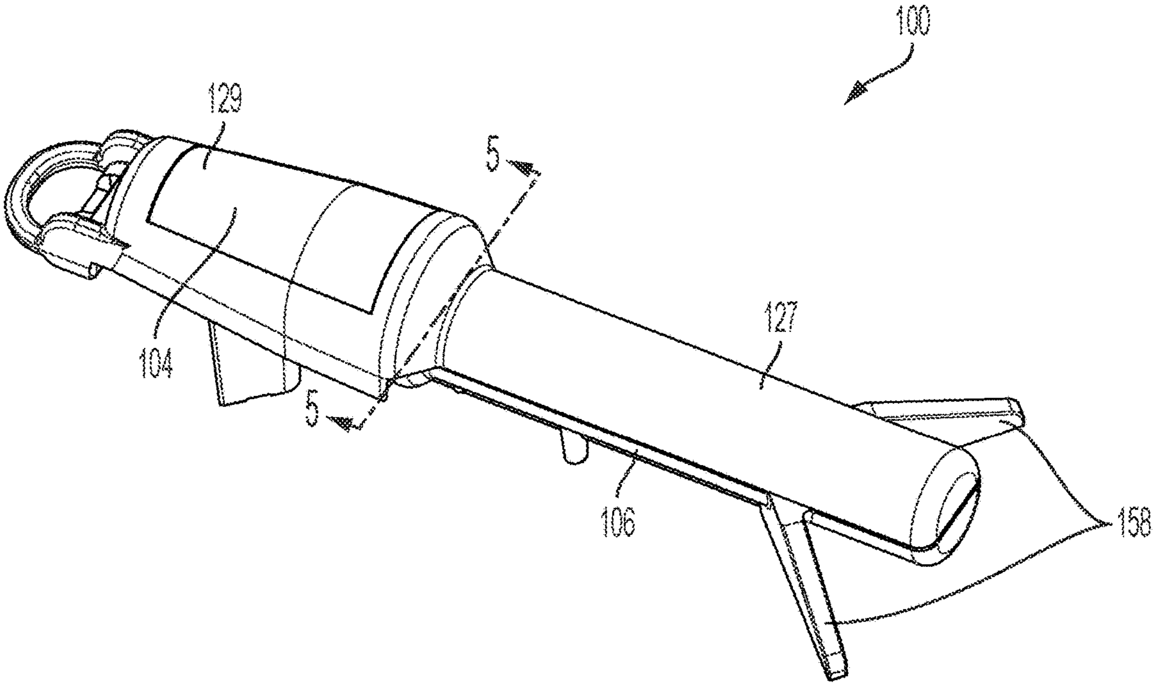
FIG. 4B is a perspective view of the ampule crush tool of FIG. 4A in a closed configuration according to one illustrative embodiment.

In some embodiments, cover portion 104 and base portion 106 include features for crushing an ampule contained within applicator 102. For example, cover portion 104 may include one or more crushers 126 (as shown in FIG. 4A) configured to crush the ampule contained within applicator 102 when cover portion 104 is moved from the open configuration to the closed configuration as described above. Relatedly, base portion 106 may include one or more crushers 124 configured to crush the ampule contained within applicator 102 when cover portion 104 is moved from the open configuration to the closed configuration. In some embodiments, only cover portion 104 includes one or more crushers 126, while in other embodiments only base portion 106 includes one or more crushers 124. In some embodiments, both base portion 106 and cover portion 104 include one or more crushers 124, 126.

Figure 7:
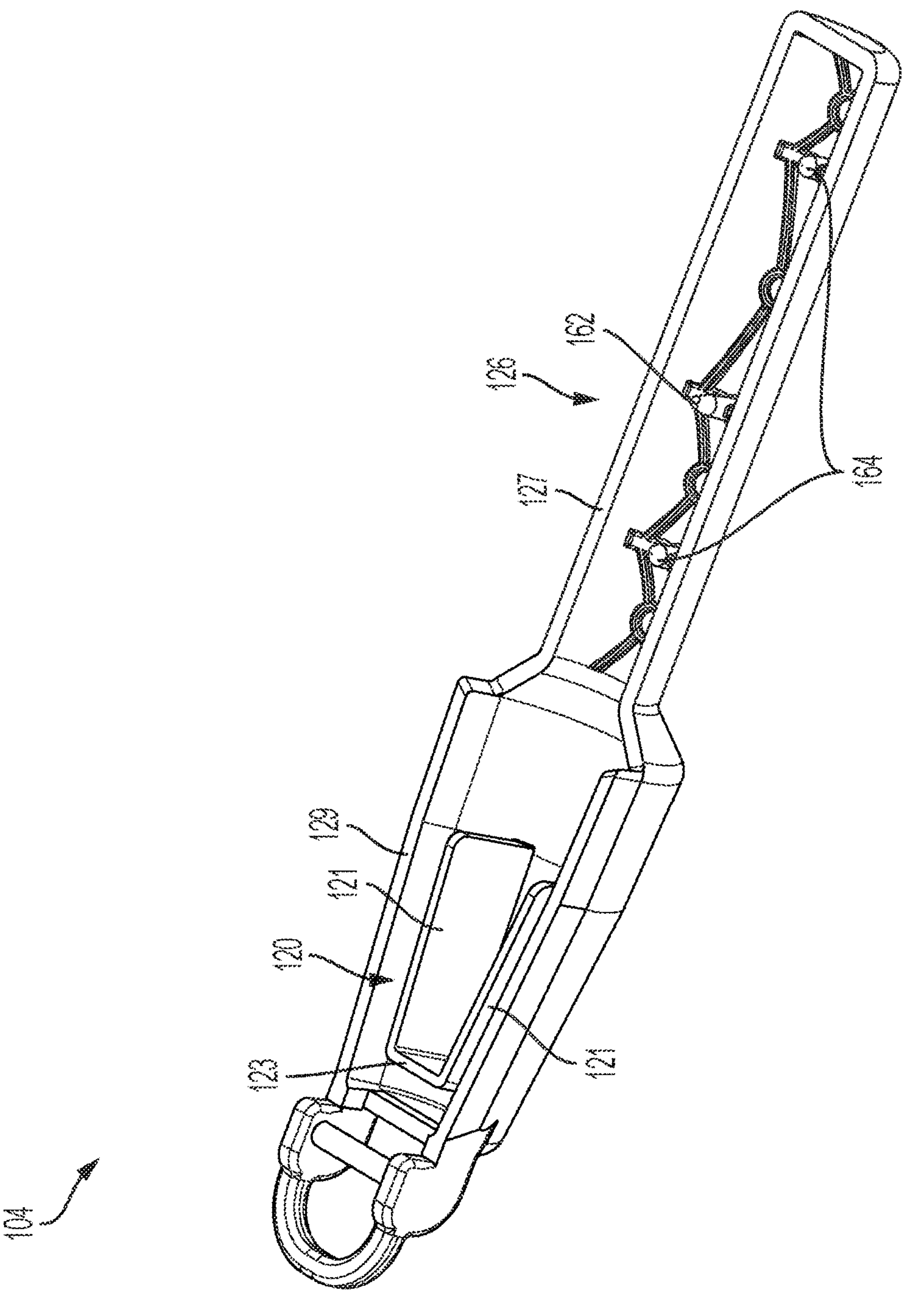
FIG. 7 is a perspective view of a cover portion of an ampule crush tool according to one illustrative embodiment.

In some embodiments, crushers 126 may take the form of pins, as shown in FIG. 7. In some embodiments, the pins may have different lengths. For example, in some embodiments, crushers 126 may include one or more long pins 162 and one or more short pins 164, wherein one or more long pins 162 extend further away from the body of cover portion 104 than one or more short pins 164. Crushers 126 may be arranged such that when applicator 102 is located within ampule crush tool 100, one or more long pins 162 make contact with a central portion of ampule 146 and one or more short pins 164 make contact with either end of ampule 146 during an ampule crushing operation. Accordingly, one or more long pins 162 may make contact with ampule 146 before one or more short pins 164, allowing one or more long pins 162 to initially crush ampule 146. Subsequently, one or more short pins 164 may make contact with ampule 146. In other embodiments, however, the pins may have the same length.

In some embodiments, the crushers may be positioned to align with certain portions of the ampule. For example, one or more crushers may be positioned to contact a central portion of the ampule, and one or more crushers may be positioned to contact the ends of the ampule. For example, in the FIG. 7 embodiment, pin 162 is flanked by two pins 164. The pin 162 is positioned to contact a central portion of an ampule, and the pins 164 are positioned to contact the ends of the ampule. The pin 162 may be positioned in a central region of the tubular portion 127, and the pins 164 may be positioned at the end regions of the tubular portion 127. The pins positioned to contact the ends of the ampule may help to fracture the ends of ampule 146. In some arrangements, intact ends of the ampule may obstruct the flow of the medicament toward the dispenser tip. The inclusion of pins that are positioned to contact the ends of the ampule may help to fracture the ends and decrease the likelihood of intact ends. However, it should be appreciated that in other embodiments, the crusher tool does not include crushers that are positioned to contact the ends of the ampule. For example, one or more crushers may be positioned to contact a central portion of the ampule. Or, in some embodiments, the ampule crush tool includes only a single crusher positioned to contact one of the ends of the ampule.

In some embodiments, the crushers 124, 126 may take on the form of ribs. The ribs may be curved, flat-edged, or any other suitable shape. In some embodiments, the shape of the ribs on the cover portion may differ from the shape of the ribs on the base portion. For example, the crushers 124 may be curved ribs, while the crushers 126 may be flat-edged ribs. In some embodiments, the reverse is true. For example, the crushers 124 may be flat edged while the crushers 126 may be curved. As will be appreciated by one of skill in the art, in some embodiments, the crushers 124, 126 may both be flat-edged, and in other embodiments, the crushers 124, 126 may be both curved.

The crushers 124, 126 may be arranged in any number of suitable patterns. For example, in some embodiments, the crushers 124, 126 may be evenly spaced along base portion 106 and cover portion 104 respectively. In other embodiments, the crushers 124, 126 may be arranged in an alternating pattern such that the crushers 124 on base portion 106 are offset from the crushers 126 on cover portion 104. In some embodiments, the crushers 124, 126 may be positioned at or near second end 116 of ampule crush tool 100. In such embodiments, the crushers 124, 126 may be positioned such that the crushers 124, 126 fracture the ampule 146, which may be located at or near second end 116 when ampule crush tool 100 is placed on a flat surface, such as surface 136.

Of course, the crushers 124, 126 need not take on the form of ribs, as many suitable types of crushers are contemplated. For example, the crushers 124, 126 may take the form of spikes, hammers, blades, protrusions, or other suitable forms for crushing the ampule contained within applicator 102.

Accordingly, ampule crush tool 100 may help a clinician more easily break ampule 146 of applicator 102 as compared to breaking ampule 146 by hand (e.g., by exerting less force). Specifically, in some embodiments, using ampule crush tool 100 may reduce a force required to crush ampule 146 to about less than 5 lbf, about less than 6 lbf, about less than 7 lbf, about less than 8 lbf, about less than 9 lbf, about less than 10 lbf, about less than 11 lbf, about less than 12 lbf, about less than 13 lbf, about less than 14 lbf, or about less than 15 lbf. Combinations of the above-referenced ranges are also possible. For example, in some embodiments, ampule crush tool 100 may be configured to reduce the force required to break ampule 146 to about 5 lbf to about 15 lbf, to about 6 lbf to about 14 lbf, to about 7 lbf to about 13 lbf, to about 8 lbf to about 12 lbf, or to about 9 lbf to about 11 lbf.

In some embodiments, the ampule crush tool 100 includes a support 112 configured to allow ampule crush tool 100 to rest at an incline when placed on a flat surface 136, as shown in FIG. 2. As ampule crush tool 100 rests at an incline, applicator 102 may rest at an incline within ampule crush tool 100 as well. For example, ampule crush tool may have a first end 118 and a second end 116 opposite first end 118. In some instances, support 112 may be located at the first end 118 so as to raise first end 118 to a first elevation relative to surface 136. Thus, support 112 may position first end 118 at an elevation greater than a second elevation of second end 116 relative to surface 136. In some instances, applicator 102 rests within ampule crush tool 100 in an orientation parallel to ampule crush tool 100, e.g., parallel to a longitudinal axis A of the cavity 160 of ampule crush tool 100. Thus, as support 112 orients ampule crush tool 100 at an incline, support 112 may also orient applicator 102 at the same incline. Specifically, applicator 102 may include a first end 108 and a second end 110. First end 108 of applicator 102 may be disposed at the first end 118 of ampule crush tool 100. Similarly, second end 110 of applicator 102 may be disposed at the second end 116 of ampule crush tool 100. Thus, applicator 102 may be oriented on a similar incline as compared to ampule crush tool 100.

Such an orientation may serve to prevent a therapeutic stored in applicator 102 from being expelled during a crushing operation. For example, in some instances, the therapeutic may be stored in an ampule 146 disposed in a tube 148 of applicator 102. Thus, when inclined as shown in FIG. 2, a gravitational force G may assist in moving the therapeutic towards second end 110 of applicator 102 after the ampule 146 of applicator 102 is crushed.

In some embodiments, support 112 may be configured to incline ampule crush tool 100 relative to surface 136 by at least about 5 degrees, at least about 6 degrees, at least about 7 degrees, at least about 8 degrees, at least about 9 degrees, at least about 10 degrees, at least about 11 degrees, at least about 12 degrees, at least about 13 degrees, at least about 14 degrees, at least about 15 degrees, at least about 16 degrees, at least about 17 degrees, at least about 18 degrees, at least about 19 degrees, or at least about 20 degrees. In some embodiments, support 112 may be configured to incline ampule crush tool 100 relative to surface 136 by less than or equal to about 20 degrees, less than or equal to about 19 degrees, less than or equal to about 18 degrees, less than or equal to about 17 degrees, less than or equal to about 16 degrees, less than or equal to about 15 degrees, less than or equal to about 14 degrees, less than or equal to about 13 degrees, less than or equal to about 12 degrees, less than or equal to about 11 degrees, less than or equal to about 10 degrees, less than or equal to about 9 degrees, less than or equal to about 8 degrees, less than or equal to about 7 degrees, less than or equal to about 6 degrees, or less than or equal to about 5 degrees. Combinations of the above-referenced ranges are also possible. For example, in some embodiments, the support 112 may be configured to incline ampule crush tool 100 relative to surface 136 by about 5 degrees to about 20 degrees, or about 6 degrees to about 18 degrees, or about 7 degrees to about 16 degrees, or about 7 degrees to about 14 degrees, or about 8 degrees to about 12 degrees, or about 9 degrees to about 11 degrees, or about 9 degrees to about 10 degrees.

In some instances, ampule crush tool may also include a second support 114. Second support 114 may be disposed at second end 116 of ampule crush tool 100. As seen in FIGS. 1A, 1B, 4A and 4B, second support 114 may include two flanges 158 (e.g., legs) for stabilizing ampule crush tool 100 as it rests on surface 136. Second support 114 may be configured to have a shorter height than that of the support 112 so as to maintain the incline between first end 118 and second end 116.

In some embodiments, an ampule crush tool may be used as follows. A clinician may first place ampule crush tool 100 on surface 136. The clinician may then open ampule crush tool 100 by moving cover portion 104 and exposing base portion 106. Subsequently, the clinician may place applicator 102 within base portion 106 such that first end 108 of applicator 102 is placed into first end 118 of ampule crush tool 100, and second end 110 of applicator 102 is placed into second end 116 of ampule crush tool 100. The clinician may then close cover portion 104 over base portion 106, fracturing the ampule contained within applicator 102 as described above. Without wishing to be bound by theory, during the crushing operation, the therapeutic contained within the ampule 146 of applicator 102 may settle towards second end 110 of applicator 102 due to the force of gravity exerted on the therapeutic and the height difference between first end 108 and second and 110 of applicator 102.

In some embodiments, support 112 may be constructed as a tower support, while support 114 may be constructed as a flanged support. In other words, support 112 may be constructed to elevate first end 118 of ampule crush tool 100 above surface 136, and support 114 may be constructed to stabilize ampule crush tool 100 on surface 136. In some embodiments, only support 112 is included, and support 114 is not included, such that the second end 110 contacts the surface 136 without having any additional support besides support 112 contacting the surface 136.

Alternatively, ampule crush tool 100 may include any suitable type of support. For example, ampule crush tool need not include separate and distinct supports 112, 114. Instead, ampule crush tool 100 may include a single continuous support extending along the length of base portion 106. Such a support may be constructed to have a suitable incline, as described above. For example, the single continuous support may be wedge-shaped to provide the incline. Of course, ampule crush tool 100 need not include exactly one or two supports, as embodiments with three or more supports are also contemplated.

Figure 3:
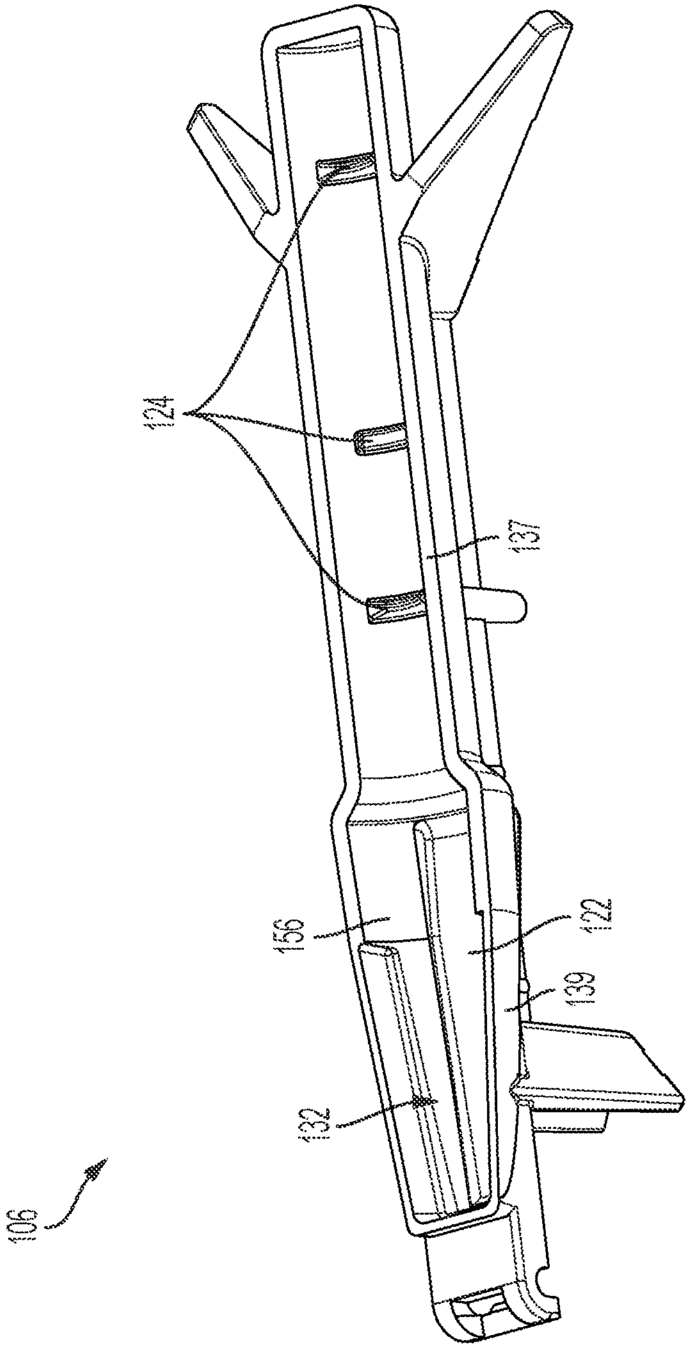
FIG. 3 is a perspective view of a base portion of an ampule crush tool according to one illustrative embodiment.

In some embodiments, ampule crush tool 100 includes features configured to collect medicament expelled from applicator 102 during an ampule crushing operation. For example, ampule crush tool 100 may include a spill reservoir 122 located within a cavity 132 of base portion 106, as shown in FIG. 3. Cavity 132 may be disposed on first end 118 of ampule crush tool 100. Cavity 132 may include a sidewall 156, and spill reservoir 122 may be indented relative to sidewall 156 of cavity 132. Based on the orientation of applicator 102 as described above, therapeutic expelled from applicator 102 during the ampule crushing operation may tend to follow a trajectory towards first end 118 of ampule crush tool 100. In some instances, ampule crush tool 100 may include a splash shield 120 (as shown in FIG. 7). Splash shield 120 may be disposed on cover portion 104 and shaped to be complementary to spill reservoir 122. Thus, splash shield 120 may be shaped to direct the medicament expelled from applicator 102 during the ampule crushing operation towards spill reservoir 122. For example, splash shield 120 may take the form of a U-shape (as in the embodiment of FIG. 7), a V-shape, or any other suitable shape. In some embodiments, as in the embodiment of FIG. 7, a U-shaped splash shield 120 may have a base 123 interconnecting two side walls 121 that are slanted. The slanted walls may form a taper that tapers in a direction facing towards the base 123. Alternatively, splash shield 120 may be made up of overlapping segments of cover portion 104 and base portion 106. Thus, rather than settling randomly within cavity 132, therapeutic expelled towards first end 118 of ampule crush tool 100 during the ampule crushing operation may tend to be collected within spill reservoir 122, which is indented relative to the sidewall of cavity 132.

In some embodiments, the volume of the spill reservoir 122 and cavity 132 is sufficient to contain the entire volume of the therapeutic in the applicator while the applicator is held within the cavity 132. In the event of a leak in the applicator, the ampule crush tool 100 may serve to catch and retain leaked therapeutic.

Figure 5:
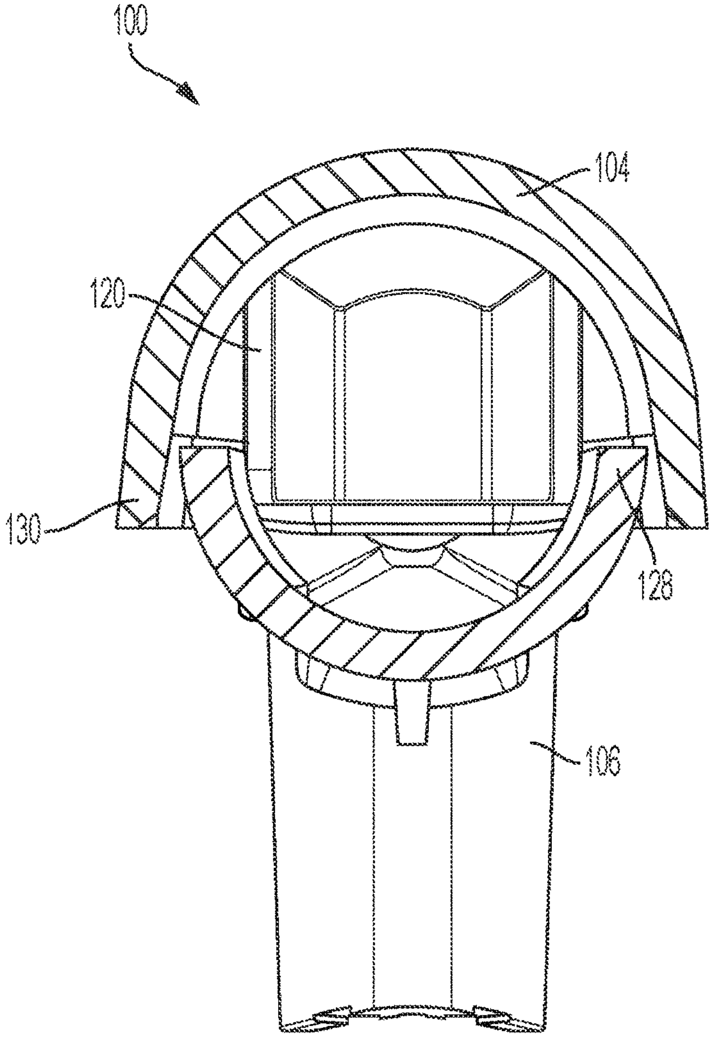
FIG. 5 is a cross sectional view of the ampule crush tool of FIG. 4B along line 5-5 according to one illustrative embodiment.

In some embodiments, the ampule crush tool may form a fully enclosed cavity when in the closed configuration to help contain expelled therapeutic. As shown in FIGS. 4A-5, ampule crush tool 100 may form a fully enclosed cavity when in the closed configuration. The fully enclosed cavity may form a complete seal relative to the external environment so as to contain the therapeutic even when the therapeutic is expelled from applicator 102 along an unpredictable trajectory. In some embodiments, cover portion 104 may include a first extending sidewall portion 128 and base portion 106 may include a second extending sidewall portion 130. To fully enclose applicator 102 within ampule crush tool 100, first extending sidewall portion 128 and second extending sidewall portion 130 may be shaped to overlap with one another when ampule crush tool 100 is in the closed configuration. Thus, when applicator 102 is placed within ampule crush tool 100 in the closed configuration, base portion 106 and cover portion 104 create a fully enclosed cavity to mitigate unwanted exposure to the therapeutic by collecting any therapeutic expelled from applicator 102 during an ampule crushing operation.

Figure 6A:
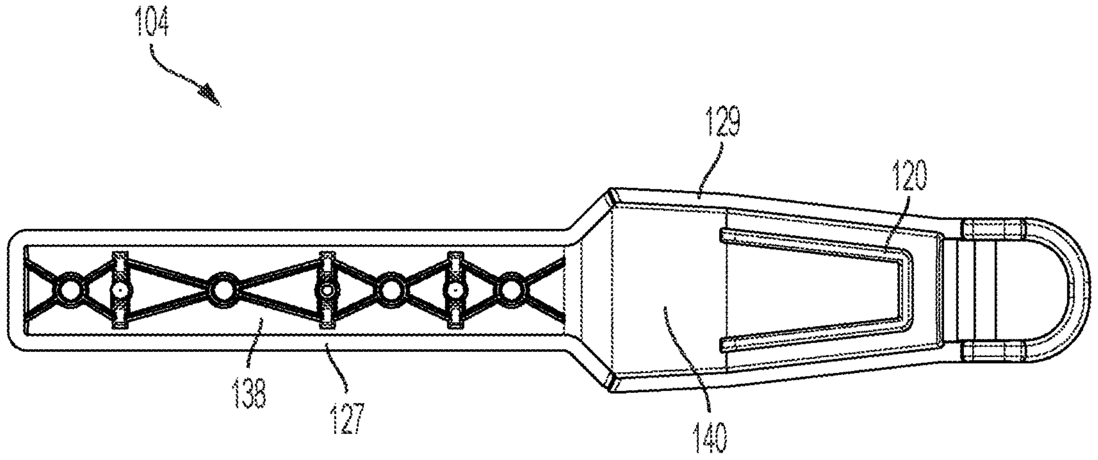
FIG. 6A is a bottom view of a cover portion of an ampule crush tool according to one illustrative embodiment.
Figure 6B:
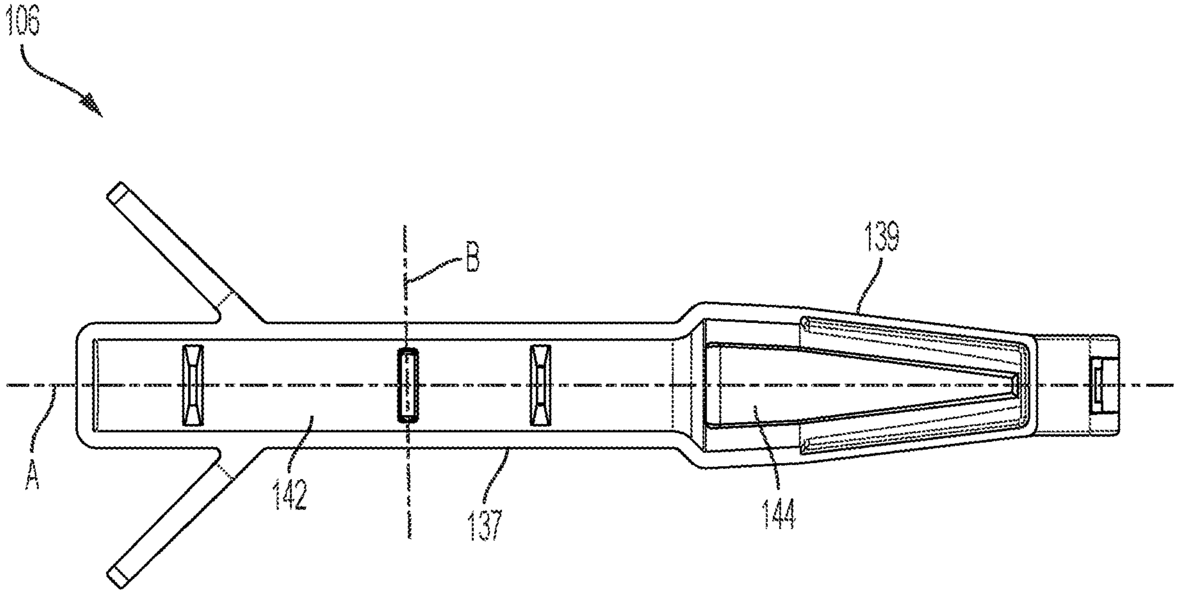
FIG. 6B is a top view of a base portion of the ampule crush tool of FIG. 6A according to one illustrative embodiment.

In some embodiments, ampule crush tool 100 may be shaped to hold applicator 102 in a specific orientation, as shown in FIGS. 6A-6B. For example, cover portion 104 may include a first cavity portion 138 and a second cavity portion 140. First cavity portion 138 may be shaped to accommodate a tube end (e.g., second end 110) of applicator 102, while second cavity portion 140 may be shaped to accommodate a dispensing end (e.g., first end 108) of applicator 102. Similarly, base portion 106 may include a first cavity portion 142 and a second cavity portion 144. First cavity portion 142 may be shaped to accommodate a tube end (e.g., second end 110) of applicator 102, while second cavity portion 144 may be shaped to accommodate a dispensing end (e.g., first end 108) of applicator 102. First cavity portion 138 of cover portion 104 may be shaped to fit over first cavity portion 142 of base portion 106. Similarly, second cavity portion 140 of cover portion 104 may be shaped to fit over second cavity portion 144 of base portion 106. Thus, ampule crush tool may be shaped so as to orient applicator 102 such that the dispensing end (e.g., first end 108) of applicator 102 is located at first end 118 of ampule crush tool 100 and to orient applicator 102 such that the tube end (e.g., second end 110) is located at second end 116 of ampule crush tool 100.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a “user.” It should be appreciated that a “user” need not be a single individual, and that in some embodiments, actions attributable to a “user” may be performed by a team of individuals and/or an individual in combination with computer-assisted tools or other mechanisms.

Use of ordinal terms such as “first,” “second,” “third,” etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of “including,” “comprising,” or “having,” “containing,” “involving,” and variations thereof herein, is meant to encompass the items listed thereafter and equivalents thereof as well as additional items.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An ampule fracture device comprising:

a body having a first end and a second end; and a support configured to incline the first end of the body at a first height vertically above a second height of the second end of the body when the ampule fracture device is rested on a flat surface and while the device is actuated to fracture an ampule, wherein the body is configured to hold a medicament applicator containing the ampule at an incline based at least in part on a difference between the first and second heights such that an outlet of the applicator is positioned at a greater height than the ampule of the applicator.

2. The ampule fracture device of claim 1, further including a cover movable relative to the body, wherein the cover includes at least one rib configured to crush the ampule when the cover is moved towards the body.

3. The ampule fracture device of claim 1, wherein the support includes a first tower portion and a second flanged portion, wherein the first tower portion is disposed on the first end of the body and the second flanged portion is disposed on the second end of the body.

4. The ampule fracture device of claim 3, wherein the first tower portion reaches a third height vertically above a fourth height of the second flanged portion relative to the surface.

5. The ampule fracture device of claim 1, wherein the body includes a plurality of ribs having curved edges configured to crush the ampule.

6. The ampule fracture device of claim 1, further comprising a cover, wherein the cover includes a plurality of ribs having flat edges configured to crush the ampule.

7. The ampule fracture device of claim 5, wherein the plurality of ribs having curved edges are disposed on the second end of the body.

8. The ampule fracture device of claim 1, further comprising a cavity disposed on the first end of the body, the cavity configured to receive at least a distal end of the medicament applicator, the distal end including a dispenser tip, wherein the cavity includes a sidewall and a reservoir that is recessed relative to the sidewall, the reservoir being configured to collect a medicament expelled from the ampule during an ampule fracturing operation.

9. The ampule fracture device of claim 1, wherein the body includes a base portion having a first cavity and a cover portion having a second cavity, wherein the cover portion and the base portion are moveable relative to one another to form an open configuration and a closed configuration, wherein, in the closed configuration, the cover portion covers the base portion, and the first cavity and the second cavity form a closed enclosure.

10. The ampule fracture device of claim 1, further comprising a cavity configured to receive the medicament applicator, wherein the cavity includes a first portion and a second portion, the first portion shaped and positioned to receive a dispensing end of the medicament applicator, and the second portion shaped and positioned to receive a tube end of the medicament applicator; the first portion having a tapered shape, and the second portion having a cylindrical shape.

11. A method of fracturing an ampule comprising:

placing a tool on a flat surface, the tool comprising a body having a first end and a second end and a support configured to incline the first end of the body at a first height vertically above a second height of the second end of the body when the tool is placed on the flat surface;

placing a medicament applicator having an ampule within a cavity of the tool; and actuating the tool to fracture the ampule while the tool holds the medicament applicator at an inclined angle relative to the flat surface, wherein the inclined angle is based at least in part on a difference between the first and second heights such that an outlet of the medicament applicator is positioned at a greater height than the ampule of the applicator.

12. The method of claim 11, further comprising removing the medicament applicator from the cavity of the tool at the inclined angle to retain medicament within the medicament applicator.

13. The method of claim 11, wherein actuating the tool to fracture the ampule causes medicament from the ampule to be expelled out of the medicament applicator.

14. The method of claim 13, further including preventing at least a portion of the medicament from expelling when the tool is actuated to fracture the ampule.

15. The method of claim 13, further including collecting the expelled medicament within the cavity.

16. The method of claim 11, wherein fracturing the ampule with the tool comprises moving a cover portion of the tool from an open configuration to a closed configuration.

* * * * *